United States Patent [19]

Nitadori

[11] 4,237,737
[45] Dec. 9, 1980

[54] ULTRASONIC IMAGING SYSTEM
[75] Inventor: Kazuhiko Nitadori, Tokyo, Japan
[73] Assignee: Oki Electric Industry Co. Ltd., Tokyo, Japan
[21] Appl. No.: 941,472
[22] Filed: Sep. 12, 1978
[30] Foreign Application Priority Data
 Sep. 14, 1977 [JP] Japan .................................. 52-109977
[51] Int. Cl.³ ........................................... G01N 29/00
[52] U.S. Cl. ......................................... 73/625; 367/7
[58] Field of Search ..................... 367/7, 12, 103, 105, 367/108; 73/625, 626, 628; 340/5 MP, 1 P, 3 R; 128/2 V, 660

[56] References Cited
U.S. PATENT DOCUMENTS

| | | | |
|---|---|---|---|
| 3,794,964 | 2/1974 | Katakura .......................... | 340/5 MP |
| 3,918,025 | 11/1975 | Koshikawa et al. ................... | 73/626 |
| 3,919,683 | 11/1975 | Itamura et al. ........................ | 73/626 |
| 3,953,825 | 4/1976 | Kino et al. ......................... | 340/5 MP |

OTHER PUBLICATIONS

"Acoustic Imaging", G. Wade, Plenum Press, pp. 170-181, 1976.
"Acoustical Holography", vol. 3, A. F. Metherell, Plenum Press, pp. 191-209, 1971.

Primary Examiner—Stephen A. Kreitman
Attorney, Agent, or Firm—Armstrong, Nikaido, Marmelstein & Kubovcik

[57] ABSTRACT

An ultrasonic imaging system is provided for forming an orthographic and a tomographic image of an object. The system comprises a receiving transducer array having a plurality of elements positioned at the lattice points of a parallelogram and a transmitting transducer array having a plurality of elements arranged in a straight line parallel to one side of the parallelogram at a period equivalent to the length of the side. A receiving beam former compensates for the delay time of the received signal for each element in the receiving transducer array and adds the compensated signals for all the elements. The receiving beam former comprises a quadrature demodulator which decomposes the output of a receiving transducer element into the inphase component and the quadrature component of a transmitting carrier signal. The beam former also includes means for delaying the components, means for performing the complex multiplication of the delayed components, means for adding the real parts of the output of the complex multiplication means for all channels, means for adding the imaginary parts of the output of the complex multiplication means for all channels, a pair of square circuits for providing the square of the real sum and the imaginary sum respectively, and an adder for adding the outputs of the square circuits. Further, means are provided for extracting the received beams in accordance with the timing of the transmitted beam and are provided for displaying the extracted received beams thereby forming an image.

1 Claim, 8 Drawing Figures

ULTRASONIC IMAGING SYSTEM

BACKGROUND OF THE INVENTION

The present invention relates to an ultrasonic imaging system by which both orthographic images and tomographic images of high resolution can be obtained, in particular, relates to such an apparatus employing only a few transducers.

Some of the application fields of the present invention are the medical field, sonar, and non-destructive inspection.

There have been two kinds of conventional ultrasonic imaging systems having a three-dimensional imaging function capable of obtaining orthographic and tomographic images simultaneously. The first one employs an acoustic lens and a plane transducer array for both transmission and reception, and scans an object by sequentially switching on and off the transducer elements in the array. The second one employs a variable delay line and plane transducers for transmission and reception, and scans electronically the directions and the focal distance of the transmitting and receiving beams (for instance, "Acoustic Imaging" by G. Wade, Plenum Press (1976), PP171–181).

However, the prior ultrasonic imaging systems have the disadvantage that a plane transducer array must have almost the same number of elements as the number of picture cells of an object. Therefore, the number of transducer elements becomes enormous when an image of high resolution must be obtained, thus, the system is almost impracticable. Further, the first prior art has the disadvantage that dynamic focusing is not possible for tomographic imaging since the focal distance is fixed, although the signal processing is simple since the image is obtained by the image formation of the acoustic lens. The impossibility of dynamic focusing restricts the bearing resolving power. The second prior art can perform dynamic focusing, but the signal processing is complex, the size of the circuitry is large, and in fact, the second prior art is almost impracticable.

SUMMARY OF THE INVENTION

It is an object, therefore, of the present invention to overcome the disadvantages and limitations of prior ultrasonic imaging systems by providing a new and improved ultrasonic imaging system.

It is also an object of the present invention to provide an ultrasonic imaging system employing a small scale transducer array having a controllable focal distance and provide an orthographic and/or tomographic images of high resolution. The above and other objects are attained by an ultrasonic imaging system comprising a receiving transducer array having a plurality of transducer elements positioned at the lattice points of a parallelogram, a transmitting transducer array having a plurality of transducer elements arranged on the straight line parallel to one side of said parallelogram at a period equivalent of the length of said side, means for applying an electrical signal having a delay time defined for each elements to said transmitting transducer array to project a focused acoustic pulse to an object, said receiving transducer array receiving the reflected sound waves from said object, means for compensating the delay time of the received signals of each elements in the receiving transducer array and adding the compensated signals of all the elements, means for extracting the received beams at the timing of the transmitted beam, and means for displaying the extracted image.

BRIEF DESCRIPTION OF THE DRAWINGS

The foregoing and other objects, features, and attendant advantages of the present invention will be appreciated as the same become better understood by means of the following description and accompanying drawings wherein.

DESCRIPTION OF THE PREFERRED EMBODIMENTS

Figure 1:
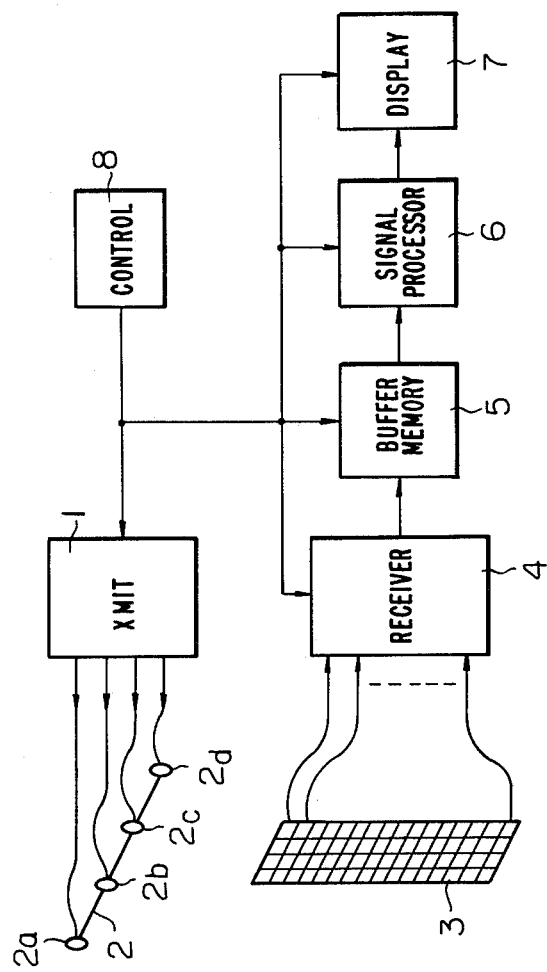
FIG. 1 illustrates a block diagram of an embodiment under the present invention.

FIG. 1 shows the block diagram of the ultrasonic imaging system according to the present invention. In the figure, the reference numeral 1 is an ultrasonic wave transmitter, 2 is a transmitting transducer array, 3 is a receiving transducer array, 4 is an ultrasonic wave receiver, 5 is a buffer memory, 6 is a signal processor, 7 is a display unit and 8 is a control unit.

The transmitter 1 generates a plurality of channels of sine-wave pulses, upon receipt of a command from the control unit 8. Each pulse signal of each channel has a predetermined amplitude, a predetermined phase and a predetermined pulse width. Those pulse signals are applied to each element of the transducer array 2a, 2b, 2c and 2d, respectively. Accordingly, a plurality of transmitting fan beams are generated from the transducer array 2. The transmitting fan beams are reflected by an object which is positioned in the space scanned by said fan beam, and the reflected acoustic beam is received by the receiving transducer array 3. The receiving transducer array 3 converts the acoustic energy to an electrical signal, which is applied to the ultrasonic wave receiver 4.

Figure 2:
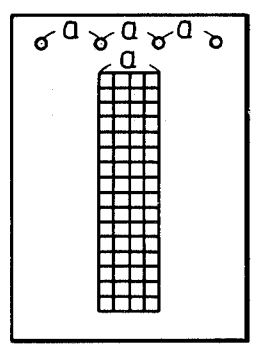
FIG. 2 illustrates a configuration of the transmitting transducer array 2 and the receiving transducer array 3 already illustrated in FIG. 1.

It is supposed that each element of the receiving transducer array 3 is positioned at the lattice point of the orthogonal coordinates system as shown in FIG. 2, and in the present embodiment, four elements are provided on each horizontal line, and sixteen elements are provided on each vertical line, thus, 64 elements are provided in total in the receiving array 3. The horizontal length of the receiving array 3 is supposed to be (a), which is equal to the period of the transmitting elements, as shown in FIG. 2.

It should be appreciated that the transmitting transducer array has only four elements, all of which are positioned on a single horizontal line. It should be appreciated that the receiving array is not restricted to a rectangular form as shown in FIG. 2, but general parallelogram is possible, and in that case, the transmitting transducer array is positioned on the straight line parallel to one of two sides of the parallelogram.

The receiver 4 amplifies the signal obtained from the transducer array 3, demodulates the signal through quadrature demodulation, and obtains the in-phase and the quadrature components. Those components are sampled and converted to a digital signal, which is stored in the buffer memory 5. It is supposed that the buffer memory 5 stores all the receiving signals obtainable in a single transmission. The signal processor 6 selects the necessary signals from those received, provides the image regeneration operation, and obtains the picture elements on a single or a plurality of scanning lines. The regenerated picture elements are applied to the display unit 7, which displays the picture signals in a predetermined format. Then, in order to obtain the picture elements on different scanning lines, the direction of the transmission beam is changed and the above operation is repeated, until all the picture elements for a whole screen are obtained. In the above course, the control unit 8 controls the operation of the system by providing the direction and the focal distance of the transmitting beam, and the parameters for the operation of the system, to each part of the apparatus.

As illustrated in FIG. 2, the transmitting transducer array 2 and the receiving transducer array 3 are arranged on the lattice points of the orthogonal coordinates system on the single plane. That is to say, the coordinates of the center of the transmitting transducer elements are shown below.

$$y_t = 0, \quad x_t = mL_x \text{ (where } m = 0, 1, \ldots, M_x - 1\text{)}$$

And the coordinates of the center of each receiving elements are shown below.

$$x_r = x_{r0} + mL_x/N_x \text{ (where } m = 0, 1, 2, \ldots, N_x - 1\text{)}$$

$$y_r = y_{r0} + nL_y/N_y \text{ (where } n = 0, 1, 2, \ldots, N_y - 1\text{)}$$

where $M_x$ represents the number of transmitting elements (in the present embodiment $M_x = 4$), $L_x$ and $L_y$ are the length in the horizontal and the vertical directions respectively, $N_x$ and $N_y$ are the numbers of the colums and of the rows of the receiving transducer array (in the embodiment $N_x = 4$, and $N_y = 16$).

Figure 4:
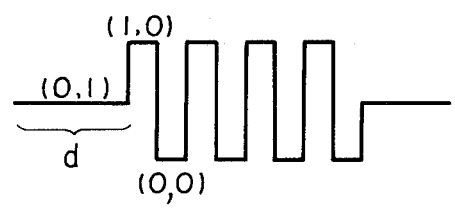
FIG. 4 illustrates a transmission signal wave of one of the channels of the transmitter.
Figure 3:
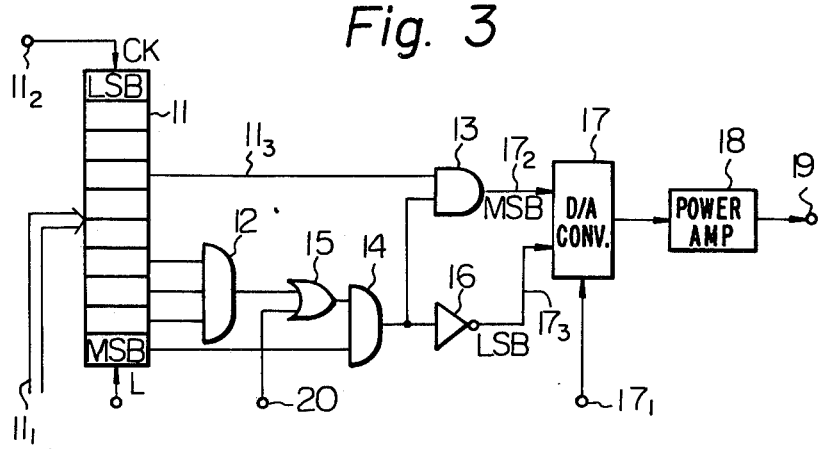
FIG. 3 illustrates details of one of the channels of the transmitter 1 illustrated in FIG. 1.

FIG. 3 shows the detailed block diagram of one of the transmitting channels of the transmitter 1 already illustrated in FIG. 1. In FIG. 3, the reference numeral 11 is a binary counter, 12, 13 and 14 are AND circuits, 15 is an OR circuit, 16 is an inverter, 17 is a multiplying type digital-to-analog converter having two input bits, $17_1$ is an analog input terminal of the DA converter 17, $17_2$ and $17_3$ are MSB (Most significant bit) and LSB (Least significant bit) input lines of the DA converter 17, 18 is a power amplifier, 19 is an output terminal, 20 is an input terminal of the pulse width control signal. It is supposed that the desired delay time for each transmission channel is calculated beforehand based upon the steering angle and the focal distance of the transmission beam obtained from the control unit 8. The result of the delay time is divided by 1/16 of the $1/f_c$ (where $f_c$ is the carrier frequency of the transmission signal). The quotient is represented by a binary number which is preset in the binary counter 11 of the corresponding channel via the data input terminal $11_1$. Upon completion of presetting of the binary counters of all the channels, the clock signal the frequency of which is 16 times of the carrier wave frequency $f_c$ is applied to the clock input terminal $11_2$ of all the channels, then each binary counter is incremented. It should be appreciated that in the course of that process, the rectangular waves repeating at a frequency of $f_c$ are obtained on the output line $11_3$ which is the fourth bit counting from the LSB. However, at the initial stage, the MSB output of the binary counter 11 being zero, the AND circuits 14 and 13 close, thus, the digital inputs $17_2$ and $17_3$ of the DA converter 17 are (0,1). When the binary counter 11 exceeds the all zero state and becomes all-"1"-state, the AND circuits 13 and 14 open, and the digital inputs $17_2$ and $17_3$ of the DA converter 17 repeats (1,0) and (0,0). That is to say, for the output of the DA converter 17, the transmitting signal with the frequency $f_c$ as illustrated in FIG. 4 is obtained in the form of the ternary rectangular wave with a predetermined delay time (d). Of course the delay time (d) is defined by the initial content of the counter 11. The clock signal at the terminal $11_2$ stops before the binary counter 11 returns to its initial state and the first operation is closed. In this case, if "1" is applied to the pulse width control input terminal 20, the pulse width at the output of the DA converter 17 is 32 cycles of the carrier wave signal, and if "0" is applied to that terminal 20, the pulse width is 4 cycles of the carrier wave signal. Thus, the pulse width of FIG. 4 can be controlled. Further, the analog signal applied to the analog input terminal $17_1$ can control the amplitude of the output signal of the DA converter 17 based upon the multiplication function of the DA converter. Accordingly, the output of the DA converter 17 can be utilized as transmitting signal. Although the signals generated by the DA converter 17 is of rectangular waves, they are changed to a form of sine wave, as the transmission bandwidth of the power amplifier 18 and the transmitter transducer is limited. It should be appreciated that the transmitter in FIG. 3 can be used not only under the present invention but also can be widely used for the formation of other transmitting beam where phased array is employed.

Figure 5:
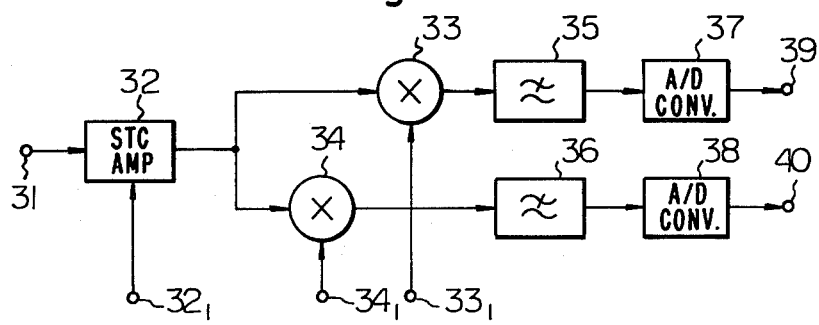
FIG. 5 illustrates details of one of the channels of the receiver 4 illustrated in FIG. 1.

FIG. 5 shows the detailed block diagram of each channel of the receiver 4 in FIG. 1. The receiving transducer signal is applied to the input terminal 31 which is connected to the STC amplifier 32. The amplifier 32 amplifies the input signal to an appropriate level, and the output of the amplifier 32 is divided to two components, in-phase component and quadrature component, by the quadrature demodulator comprising the multipliers 33, 34 and the low pass filters 35 and 36. Each components are converted to a digital form by the analog-to-digital converters 37 and 38 respectively, and are applied to the buffer memory 5 in FIG. 1 through the output terminals 39 and 40. The STC input terminal $32_1$, and the reference carrier wave input terminals $34_1$ and $33_1$ are common to all the channels. The signal at the terminal $32_1$ is the gain control signal of the STC amplifier, and the signals at the terminals $34_1$ and $33_1$ are sine wave signals of the frequency $f_c$, each are in-phase with the transmission carrier wave signal and 90° phase delay signal.

The apparatus in FIG. 1 can operate in either of the two different operational modes, i.e. orthographic imaging or tomographic imaging. These two modes are switched through the operation of the control unit 8 in FIG. 1.

In the case of orthographic image mode, transmission signal is transmitted to the transmitting transducer array 2 from the transmitter 1 so that the signals will be brought to focus (so that the acoustic wave from each element becomes in-phase) at one point on a plane after traveling a prescribed distance (the distance for observation) in the direction at right angle to the transmitting transducer array. Provided that, in this operation, the transmitting pulse should be of wider width (32 cycles). In the course of this operation, multiple numbers of fan beams are generated because of the regularity of the transmitting transducer array. These beams simultaneously focus on the multiple longitudinal lines on the target object as illustrated in FIG. 6(a), and acoustic pressure on these lines become high. The traveling direction of the acoustic wave is at right angle to the surface of the paper of the diagram.

Figure 6:
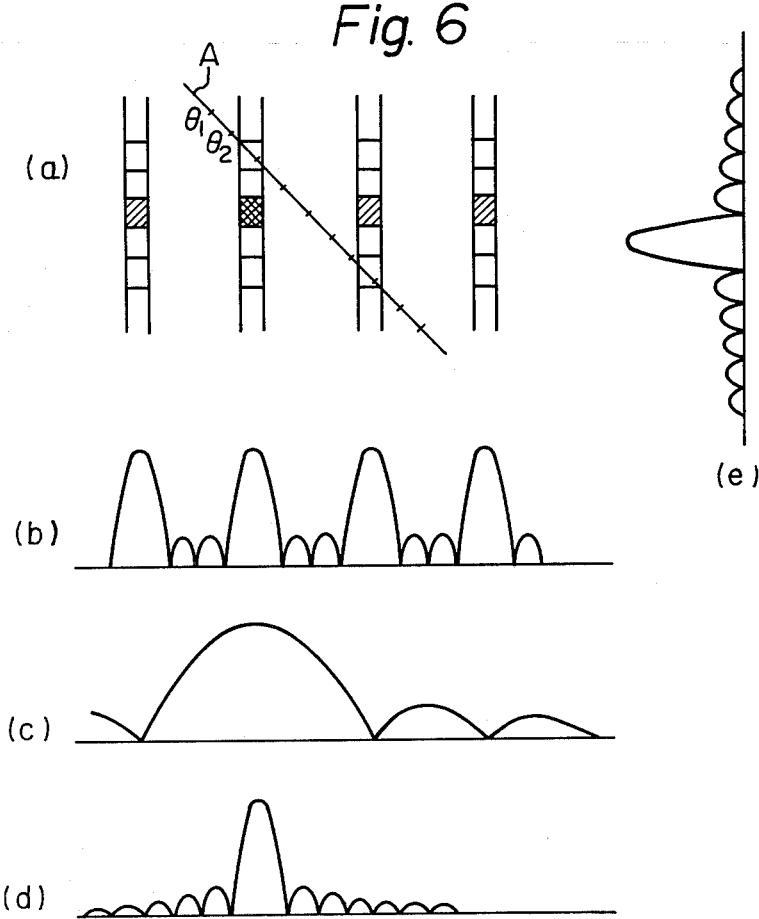
FIGS. 6(a)–(e) illustrates wave forms for the explanation of the operation of the present invention.

FIG. 6 (b) illustrates the acoustic pressure distribution (transmitted beam pattern) on the curved surface on the horizontal axis. If there is a substance that reflects sounds on the surface of the reflecting target, the echo arrives at the receiving transducer 3 and is received. This signal is converted into digital signal by the receiver 4, and only those signals reflected from the neighboring range of the reflecting body are selected on time basis and are temporarily stored in the buffer memory 5. Then, the signal processor 6 reads out these signals from the buffer memory 5 and cumulatively add these by each receiving channel. Then the secondary phase compensation is provided to the signals which are cumulatively added so that the receiving beam will be brought to focus at one of the foci of the transmitting beam, and then provide the two dimensional Fourier conversion of $(N_x \times N_y)$th order.

The above process in the orthogonal imaging is mathematically explained below.

It is supposed that the length between the transmitting and/or receiving transducers and the target is (z) and the x-coordinate of the focal point of the transmitting beam is $(x_i)$, then the sine wave signal having the complex amplitude shown below must be transmitted.

$$S_t(x_t;x_i) = \exp\left(-i\frac{\pi}{\lambda z}(x_t^2 - 2x_ix_t)\right) \quad (1)$$

In the formula (1) the phase delay is expressed as $$-\pi(x_t^2 - 2x_ix_t)/\lambda z$$

and $\lambda$ is the wave length. In this case, the beam focuses at the point $(x_i')$ which satisfies the formula below because of the periodicity of the transmitting beam.

$$x_i' = x_i + m\lambda z/L_x, \text{ (where m is an integer)}$$

The received signal corresponding to the transmitting signal of the formula (1) is supposed to have the complex amplitude $S_r(x_r,y_r;x_i)$, which is read out from the buffer memory 5 and is accumulated in each receiving channel. For that signal $S_r(x_r,y_r;x_i)$, the second order phase compensation is performed according to the formula (2) below.

$$S_{rp}(x_r,y_r;x_i) = S_r(x_r,y_r;x_i) \cdot \exp\left(-i\frac{\pi}{\lambda z}(x_r^2 + y_r^2 - 2x_ix_r)\right) \quad (2)$$

For the result of the formula (2), the two dimensional Fourier transform of $(N_x \times N_y)$'th order defined by the formula (3) is performed to obtain the $N_x \times N_y$ number of independent receiving beams.

$$f(x_1 + m\lambda z/L_x, y_i + n\lambda z/L_y) = \quad (3)$$
$$\sum_{p=0}^{N_x-1} \cdot \sum_{q=0}^{N_y-1} \cdot S_{rp}(x_r,y_r;x_i) \cdot \exp\left(i2\pi\left(\frac{mp}{N_x} + \frac{nq}{N_y}\right)\right)$$

Through the above operation, $(N_x \times N_y)$ numbers of independent receiving beams are formed each having a beam pattern as illustrated in FIG. 6 (c) in horizontal direction, and in FIG. 6 (e) in longitudinal direction. Provided the peak points of the transmitting beam pattern in FIG. 6 (b) coincide with the zero points of the receiving beam illustrated in the diagram. The receiving beam in the horizontal direction has a broad width, but combined with the transmitting beam, a sharp beam similar to the longitudinal direction such as shown in FIG. 6 (d) can be obtained. That is, the receiving beam output of $(N_x \times N_y)$ numbers obtained from the above signal processing, are the picture element signals that match with each square within the range in the belt-shaped zone in FIG. 6 (a). Therefore, if the intensity of these signals are converted into brightness or color and are displayed in a position that corresponds to the position on the screen of the display unit $7_1$, the $N_y$ numbers of picture elements on the $N_x$ numbers of longitudinal lines in one complete picture are decomposed. Then, the steering of the transmitted beam is shifted to the horizontal direction by one picture element component, and transmission, reception, and signal processing are performed in the same manner as described above. Then, another $(N_x \times N_y)$ numbers of picture elements are decomposed following the same pattern of process. Thereafter, by shifting the steering of the transmitting beam and by continuing the similar pattern of process sufficient picture elements to fill the whole of the display screen can be obtained, and one complete picture of orthographic image is obtained.

Figure 7:
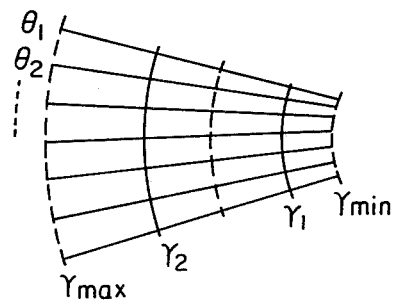
FIG. 7 illustrates an example of a display format of tomographic image.

Then, in the case of tomographic imaging mode, an intersecting line of the tomographic image to be displayed and the orthographic image are to be designated on the display screen of the orthographic image, and these lines are divided into sections of one picture element each (FIG. 6 (a) line A). These sectrices $(\theta_1, \theta_2, \ldots)$ are made steering of transmitting beam. One or several focal distances $(r_1, r_2, \ldots)$ are selected so that the depths of foci of the transmitted beams may overlap one another between the minimum distance $r_{min}$ and the maximum distance $r_{max}$ of the tomographic image to be displayed. The transmitted beams with these steerings and focal distance are generated in sequence, reception and processing of signals are performed as indicated below, and thus picture elements are decomposed. Provided narrow pulses (4 cycles) are used for transmitting signal. In this manner, sector scan image of any cross sectional surface can be obtained by the format (polar coordinate) as depicted in FIG. 7.

The transmitting beam having the steering $\theta_1$, and the focal distance $r_1$ is obtained by transmitting the signal (sine wave) from the transducer located at $(x=x_t, y=0)$ with the delay time $d(x_t) = -(x_t^2 - 2x_ix_t)/2cr_1$, where c is the sound velocity and $x_i$ is the x-coordinate of the focal point.

The reflected wave of the transmitting beam with steering $\theta_1$, and focal distance $r_1$ is quadrature demodulated at the receiver 4, is then converted into digital signal and is temporarily stored into the buffer memory 5. Responding to these receiving signals, receiving beams with steadily increasing focal distance are formed from steering $\theta_1$ and $r_{min}$ at the signal processor 6.

The receiving beam having the steering $\theta_1$ and the focal distance r is formed by delaying the signal received by the transducer located at $(x=x_r, y=y_r)$ by the quantity as follows.

$$d(x_r, y_r) = -(x_r^2 + y_r^2 - 2x_i x_r - 2y_i y_r)/2cr$$

After that, all the received signals are added to one another to obtain the receiving beam. Provided $(x_i, y_i)$ are the coordinates of the focal point. Said delay time is provided as follows.

First, the desired delay time $d(x_r, y_r)$ is divided by $T_s$ which is the sampling period of the received signal (after quadrature demodulation) in the receiver 4, and the quotient $N_d$ and the remainder $\Delta d$ are obtained. Next, the remainder $\Delta d$ is converted to the phase under the relationship $\phi(\Delta d) = 2\pi \Delta d f_c$, where $f_c$ is the frequency of the signal. The delay time $T_s N_d$ is obtained when the received signal is read out from the buffer memory 5 by shifting the address of said memory, and the delay time $\Delta d$ is substantially provided through the phase shifting.

Figure 8:
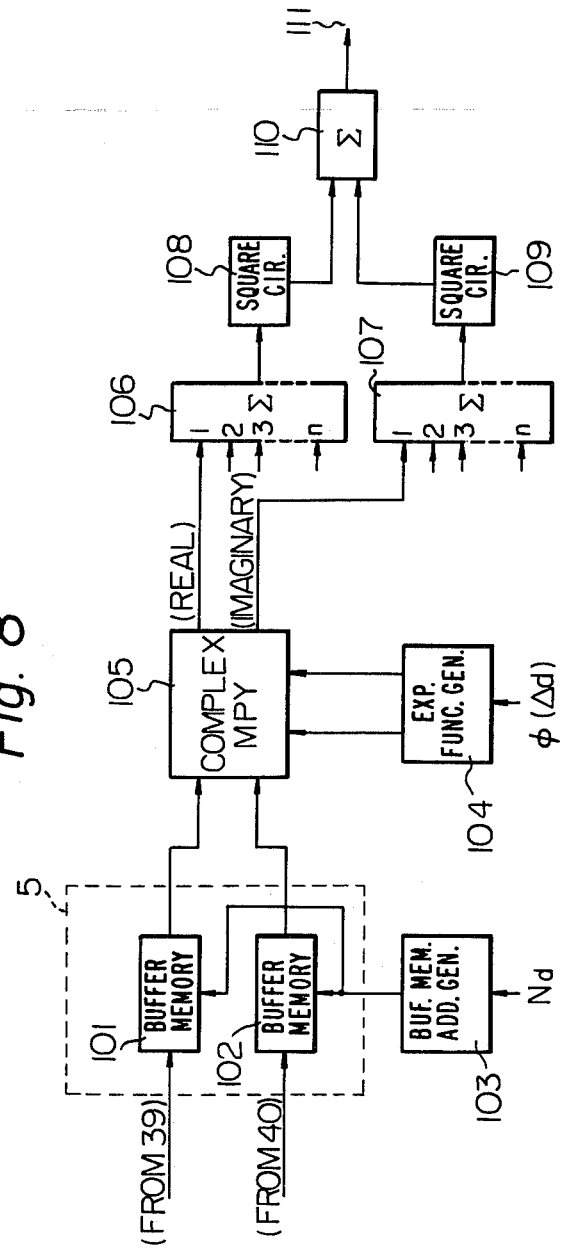
FIG. 8 shows the block diagram of a receiving beam former according to the present invention.

FIG. 8 shows the block diagram of the unit for forming the receiving beam.

In FIG. 8, the memories 101 and 102 are the same as the memory 5 in FIG. 5, and another portions in FIG. 8 are included in the signal processor 6 in FIG. 1.

The output signal of the receiver 4 in each channel is stored in the buffer memories 101 and 102 through the terminals 39 and 40. The buffer memory address generator 103 modifies the read addresses of the memories 101 and 102 according to the delay time $N_d$, and the delay time $T_s N_d$ is obtained by reading out the buffer memories 101 and 102 using said modified addresses. Also, the complex exponential function generator 104 generates the value, $$\exp(i\phi(\Delta d)) = \cos \phi(\Delta d) + i \cdot \sin \phi(\Delta d)$$

in accordance with the phase delay $\phi(\Delta d)$. The complex multiplier 105 performs the complex multiplication of the outputs of the buffer memories 101 and 102 and said function generator 104, assuming that the output of the memory 101 is real and the output of the memory 102 is imaginary. The real component and the imaginary component of the output of the complex multiplier 105 are applied to the adders 106 and 107, which receive also the corresponding signals of another channels, thus, the real and imaginary components of the delay and phase compensated signals of all the channels are added to one another in the adders 106 and 107, the output of which are squared by the square circuits 108 and 109. The outputs of the square circuits 108 and 109 are added to each other in the adder 110, the output of which is applied to the output terminal 111 as the output signal of the received beam.

It should be appreciated that the function of FIG. 8 can be accomplished by using a programmed general purpose computer although FIG. 8 disclosed the embodiment which utilizes hardware elements.

Each picture element of the tomographic image thus obtained is displayed by converting it into brightness or color on the display screen of the display unit 7 according to the format such as depicted in FIG. 7.

In the case of the tomographic imaging mode, transmission must be normally repeated each time the steering $\theta_1, \theta_2, \ldots$ of the transmitting beam changes. But if the cross sectional area is parallel to the receiving transducer array (vertical in FIG. 6 (a)), one transmission scans the directions of all the steerings of the cross-sectional area. Therefore, the steerings are not required to change. It is sufficient to switch over the focal distance by several steps in order to further the scope of observation in the direction of the depth. However, in the formation of receiving beam, for the same received signals, steerings must be changed and the process must be repeated.

As described above, according to the present invention, orthographic image or tomographic image of high resolution can be obtained by combined use of relatively small scale transmitting transducer array and receiving transducer array. Thus, the size and cost of the ultrasonic imaging system can be reduced. Contingent upon objective of its use and the configuration of the object to be observed, the present invention provides adequate data for the recognition of an object through display of orthographic image or tomographic image as preferred by switching from one to the other, or by sequentially changing the focal distances of orthographic image or cross-sectional area of tomographic image.

The present invention based on the above described embodiment can be modified in many ways. Some of them are listed below:

1. In the transmitter 1, the transmitting beam former incorporating the delay line with taps and the analog switches can be used.
2. The receiving beam former's function performed in the receiver 4, the buffer memory 5, and in the signal processor 6 can also be performed by the conventional beam former with the delay lines with taps and analog switches.
3. A scan converter can be installed between the signal processor 6 and the display unit 7. The orthographic imaging mode and the tomographic imaging mode are used by switching from one to the other. The image obtained through these operational modes can be converted into a common scan mode (e.g. raster scan). And, the images can be displayed side by side on one display screen. Similarly, a display manifesting three dimensional configuration becomes possible by simultaneously displaying an orthographic image and two tomographic images on the horizontal and the vertical cross sections.

In the course of these displays, correlation among the images can be clarified by the display on the display screen of the overlapping of the intersecting lines between the orthographic image plane and the tomographic image plane, as well as between two tomographic image planes.
4. It is possible to obtain an orthographic image that passes the point designated on one of the tomographic images and at the same time is perpendicular to this particular cross-section is obtainable. An orthographic image which contains this designated point is also obtainable. A curve is designated on a plane figure. A tomographic image on the cross section containing this particular curve is obtainable. From the above operation, detailed information on three dimensional configuration of an object is obtainable.
5. The ratio of image signal to noise can be improved by lowering the side probe level of the combined beam pattern, by providing transmitting beam shading by making the transmitting level of the output signal of each channel of the transmitter 1 unequal and by providing receiving beam shading by multiplying window function to the received signal prior to receiving beam formation; by lowering the side robe level of the combined beam pattern of the transmission and reception.

6. The transmitting transducer array and the receiving transducer array can be of any configuration provided the aperture synthesis can be effectively performed. For example, it is appropriate if the configuration of the receiving transducer array is a parallelogram while the transmitting transducer array is arranged in parallel to either side of the receiving transducer array at an interval having the same distance at the length of each side. In an extraordinary case, both arrays can assume the configuration of one straight line.

The present invention has an advantage in that it is capable of obtaining ultrasonic images of high resolution orthographic image and tomographic image of three dimensions by the use of relatively small scale equipment. Therefore, the present invention when utilized will bring about great effects in the application fields where three dimensional data have great significance e.g. ultrasonic medical diagnosis and seabed geological survey.

From the foregoing it will now be apparent that a new and improved ultrasonic imaging system has been found. It should be understood of course that the embodiments disclosed are merely illustrative and are not intended to limit the scope of the invention. Reference should be made to the appended claims, therefore, rather than the specification as indicating the scope of the invention.

What is claimed is:

1. An ultrasonic imaging system for forming an orthographic image and a tomographic image of an object comprising:
   (a) a receiving transducer array having a plurality of elements positioned at the lattice points of a parallelogram,
   (b) a transmitting transducer array having a plurality of elements arranged on a straight line parallel to one side of said parallelogram at a period equivalent of the length of said side,
   (c) means for applying an electrical signal, having a delay time defined for each element, to said transmitting transducer array to project an acoustic pulse to an object,
   (d) said receiving transducer array receiving the reflected sound waves from said object,
   (e) a receiving beam former for compensating for the delay time of the received signals of each element in the receiving transducer array and adding the compensated signals of all the elements, said receiving beam former comprising of a quadrature demodulator which decomposes the output of a receiving transducer element into the inphase component and the quadrature component of a transmitting carrier signal, means for delaying said components, means for performing the complex multiplication for the delayed components, means for adding the real parts of the output of the complex multiplication means of all the channels, means for adding the imaginary parts of the output of the complex multiplication means of all the channels, a pair of square circuits for providing the square of the real sum and the imaginary sum respectively, and an adder for adding the output of said square circuits,
   (f) means for extracting the received beams in accordance with the timing of the transmitted beam, and
   (g) means for displaying the extracted received beams thereby forming an image.

* * * * *